United States Patent [19]

Neuhaus

[11] Patent Number: Plant 7,249

[45] Date of Patent: Jun. 19, 1990

[54] POINSETTIA PLANT '13-86'

[75] Inventor: Wilhelm Neuhaus, Duisburg, Fed. Rep. of Germany

[73] Assignee: Paul Ecke Ranch, Inc., Encinitas, Calif.

[21] Appl. No.: 266,901

[22] Filed: Nov. 3, 1988

[51] Int. Cl.[5] ..... A01H 5/00

[52] U.S. Cl. ..... Plt./86

[58] Field of Search ..... Plt./86

*Primary Examiner*—James R. Feyrer

*Attorney, Agent, or Firm*—Arnold, White & Durkee

[57] ABSTRACT

Described is a new Poinsettia cultivar, designated '13-86', which is a vigorous, self-branching Poinsettia of medium height. '13-86' is distinguished by its large, bicolored pink on white flower bracts, and relatively large number of cyathia and bracts, which give the flowers a full appearance. '13-86' originated as a color sport of the red-bracted cultivar described in U.S. Plant Pat. No. 5,492.

1 Drawing Sheet

BACKGROUND OF THE INVENTION

'13-86' is a vigorous, self-branching Poinsettia of medium height and large bicolored, pink on white flower bracts. There are relatively large number of cyanthia and bracts, giving the flowers a nice full appearance. '13-86' has self-branching traits which make it desirable for branched plant production. It can be flowered in a relatively cool greenhouse, making it economical to grow commercially.

This new poinsettia cultivar originated as a color sport of the red bracted cultivar described in U.S. Plant Pat. No. 5,492, in a greenhouse in Duisburg, West Germany. This pink on white sport has all the self-branching traits and other desirable growth characteristic of the cultivar of U.S. Plant Pat. No. 5,492. After selection, vegetatively reproduction of this plant by stem cuttings for test purposes in Duisburg, West Germany, and clones of the plant were subjected to successive generations of vegetative propagation which demonstrated that its pink on white bract coloration and other distinctive characteristics hold true from generation to generation.

DESCRIPTION OF THE PHOTOGRAPHS

'13-86' is illustrated in the accompanying color photographs. The upper photo is a side view of typical unbranched plant in full flower. The lower photo is a top view of a plant showing flower and bract formation.

DESCRIPTION OF THE PLANT

The following is a detailed description of this new Poinsettia as observed in Encinitas, Calif., during December, 1987. Observations were recorded from flowering plants, grown as 3 unpinched plants per pot. The pot was 14 cm. in diameter and 11 cm. in height. Color designations were compared to the 1986 edition of the R.H.S. Colour Chart, first published in 1966 by The Royal Horticultural Society, London, England.

THE PLANT

Origin: Sport of the cultivar described in U.S. Plant Pat. No. 5,492.

Classification:

*Botanic.*—*Euphorbia pulcherrima* Willd.

*Common name.*—Poinsettia.

*Cultivar name.*—13-86'.

Form: Shrub.

Height: Medium.

Growth habit: As a single stemmed plant, upright and vigorous. In full flower, the stem in terminated by a large inflorescence, with several smaller flowering side shoots lower on the stem. Observation of 3 plants in a pot with an overall height of 40 cm. and an overall width of 46 cm. were made. The bract diameter of individual flowers was 32 cm.

Branching: Branching can be enhanced by removal of the stem tip. Then, several flowering branches with equal vigor may develop on a single plant.

Growth rate: Very fast. Rooting of stem cuttings occurs in 12–18 days under intermittent mist. The plant will flower in about ten weeks under continuous long night conditions and night temperatures of about 16–18 degrees C.

Foliage: The foliage is clean and uniformly green from bottom to top of the plant. The leaves are of medium size, leaf blades typically being about 13–15 cm. long and about 8–9 cm. wide with leaf petioles about 5–6 cm. long.

Leaf shape: Typical leaves are ovate with obtuse bases and acuminate tips. Leaf margins are mostly entire with some modest lobing and undulation.

Color:

*Upper side.*—Darker than RHS 147A.

*Under side.*—Near RHS 137C.

Retention: The foliage retention is good even under low light intensities in the consumer's home.

Bracts: Generally there are 27–30 pink on white bracts of various sizes subtending the cyathia. The primary bracts have blades typically 14–16 cm. long and 10 cm. wide with petioles about 4–5 cm. long. The bracts are somewhat rugose, more so than the parent plant (U.S. Plant Pat. No. 5,492) which only show a mild rugosity.

Shape: Bracts are ovate to mostly obovate with bases acute to mostly attenuate and tips acuminate to cuspidate. Primary bracts are mostly entire; some with modest lobing on either side of the bract. Bracts are generally longer relative to their width when compared to the parent plant (U.S. Plant Pat. No. 5,492).

Color:

*Upper side.*—White with pink marbling. White near RHS 155A, pink near RHS 51C. The pink coloration occurs in the center of the bracts along either side of the mid-vein, with the white variegation being at the bract margins.

*Under side.*—White between RHS 155A and RHS 150D, pink near RHS 51C.

Cyathia: Generally, 21–24 cyathia (flowers) are present when the plant is in "full bloom". Each cyathium is about 6–7 mm long and about 5–6 mm wide, green in color, fringed with yellow at thedistal end, unlike the parent plant which has a creamy white fringe. Usually, two bright yellow nectar cups protrude from the sides of the cyathia. The flower pedicel is also green and about 5–6 mm in length. The anthers protruding from the cyathia are white, unlike the parent plant whose anthers are red.

What is claimed:

1. A new and distinct Poinsettia cultivar, substantially as herein shown and described, distinguished by its large, bicolored pink on white flower bracts, and relatively large number of cyathia and bracts.

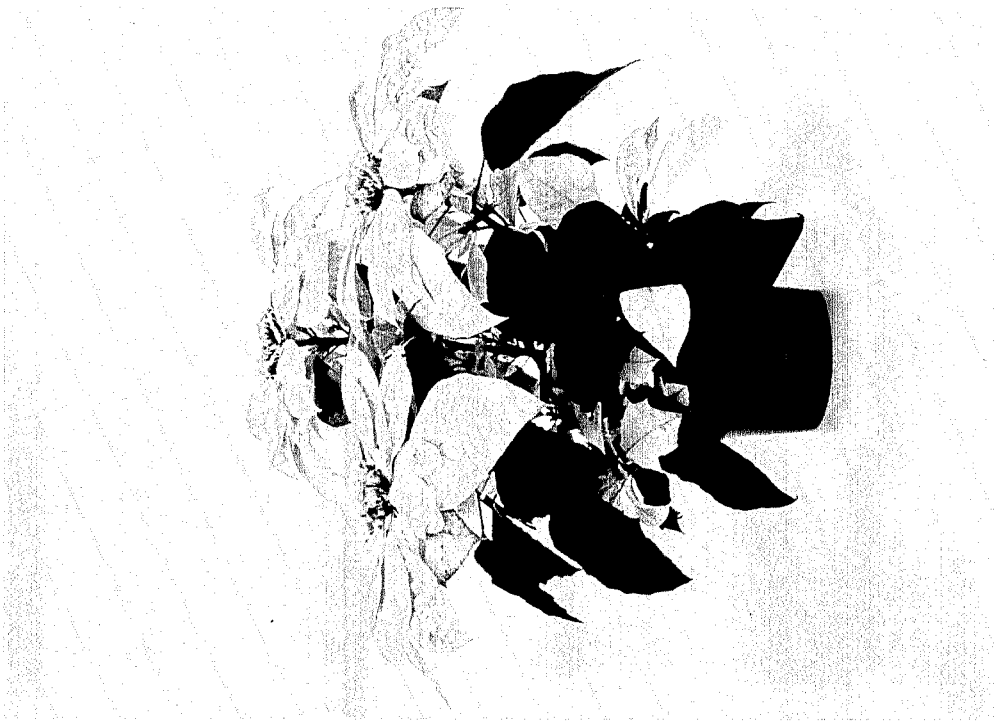
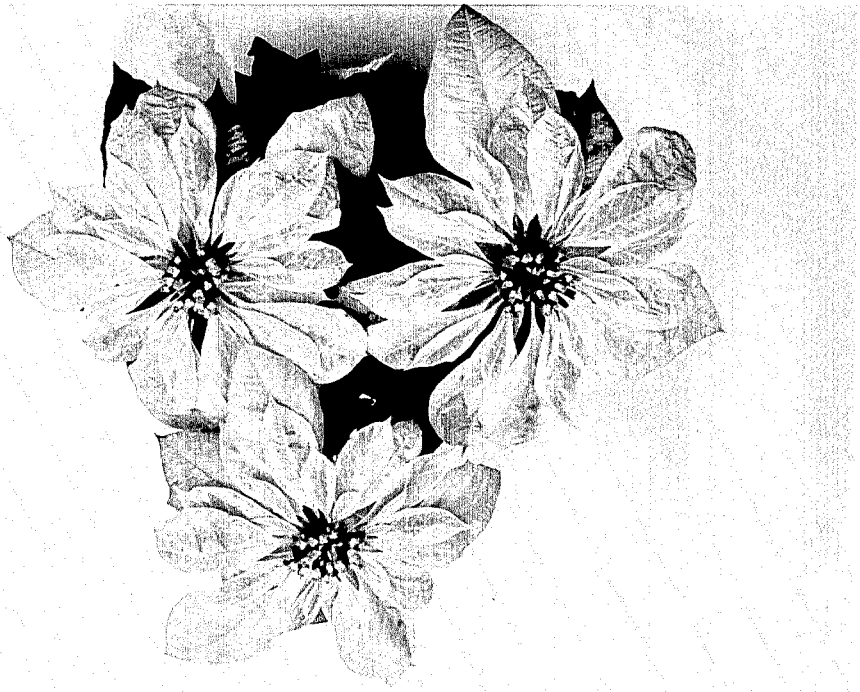

* * * * *